United States Patent [19]

Echols

[11] Patent Number: 5,449,005
[45] Date of Patent: Sep. 12, 1995

[54] REMOVABLE, SHOE INTERIOR ANKLE BRACE

[76] Inventor: Tony R. Echols, 715 W. Jackson St., Paulding, Ohio 45879

[21] Appl. No.: 171,417

[22] Filed: Dec. 22, 1993

[51] Int. Cl.$^6$ .......................... A61F 5/37; A61F 5/00; A43B 7/20
[52] U.S. Cl. ...................... 128/882; 602/23; 602/27; 36/89
[58] Field of Search .................. 128/882, 869; 602/23, 602/27, 28, 62, 63, 64, 65, 66; 36/89, 88, 140

[56] References Cited

U.S. PATENT DOCUMENTS

| | | | |
|---|---|---|---|
| 674,066 | 5/1901 | Mitchell | 602/66 |
| 1,397,095 | 11/1921 | Hamilton | 602/65 |
| 2,789,374 | 4/1957 | Planert | 36/89 |
| 3,419,974 | 1/1969 | Lange | 36/89 |
| 3,834,377 | 9/1974 | Lebold | 128/DIG. 15 |
| 4,294,238 | 10/1981 | Woodford | 602/23 |
| 4,385,456 | 5/1983 | Livernois | 36/115 |
| 5,088,478 | 2/1992 | Grim | 602/27 |

FOREIGN PATENT DOCUMENTS 2241170 8/1991 United Kingdom .................. 602/27

*Primary Examiner*—Michael A. Brown
*Attorney, Agent, or Firm*—Jacobson, Price, Holman & Stern

[57] ABSTRACT

A quarter-top to high-top athletic shoe insert including horizontally elongated, generally parallel and panel-like edge upstanding wings having corresponding front and rear ends joined at their rear ends by an integral, curved and edge upstanding bight panel portion with the inner surfaces of the rear ends of the wings and the central portion of the lower margin of the bight panel portion including fluent material filled flexible pads supported therefrom and the outer surfaces of the rear ends of the wings and the outer surface of the bight panel portion above the lower margin thereof provided with thistle-type fastening strips for coacting releasable anchoring to similar opposing thistle-type fastener strips secured to the inner surfaces of the athletic shoe top in which the insert is placed, the insert being constructed of stiff, but somewhat flexive material.

12 Claims, 2 Drawing Sheets

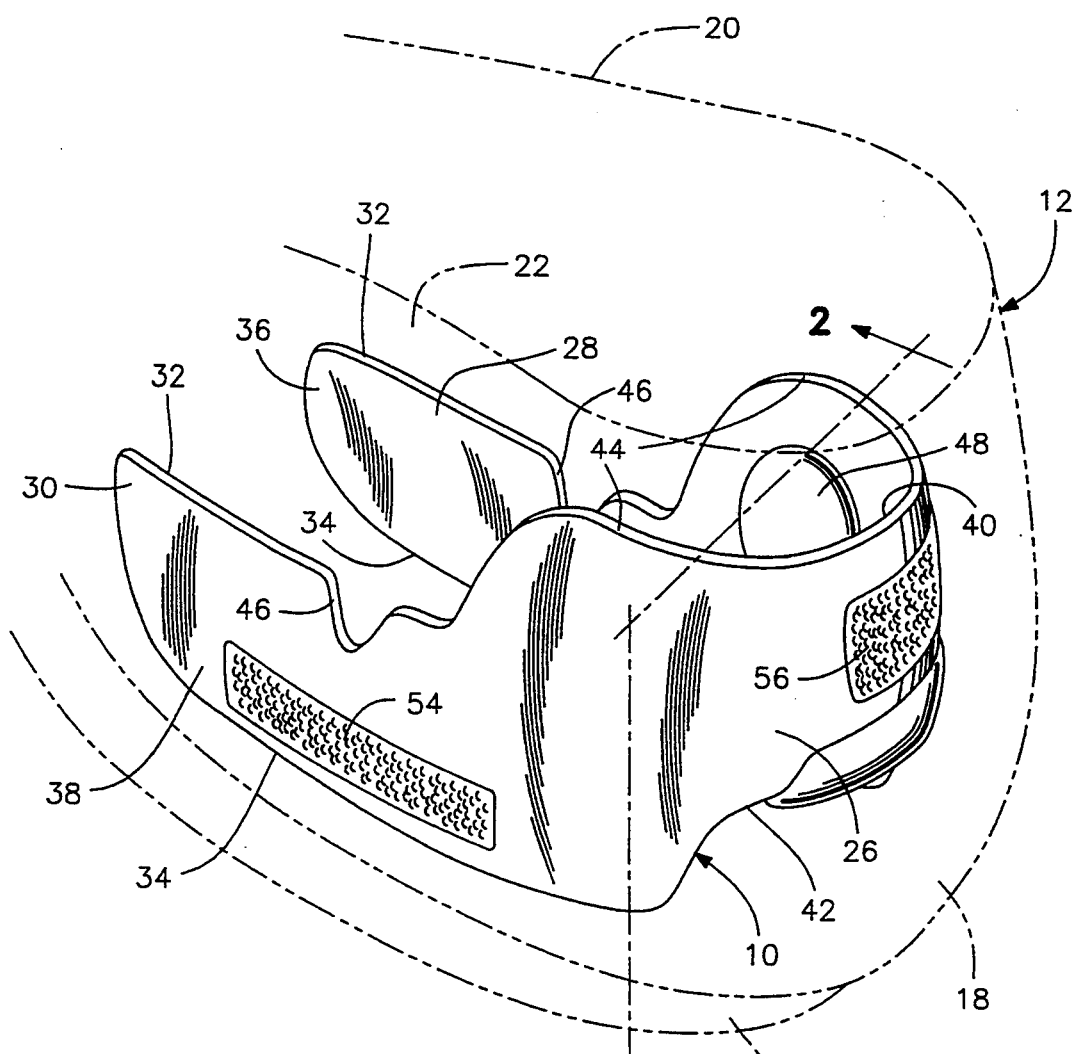
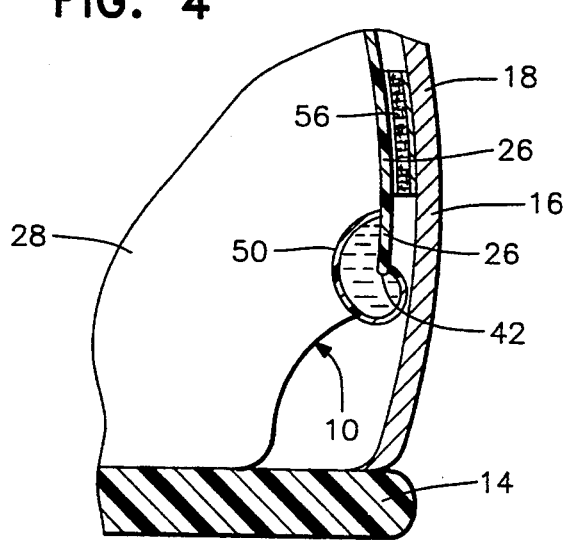

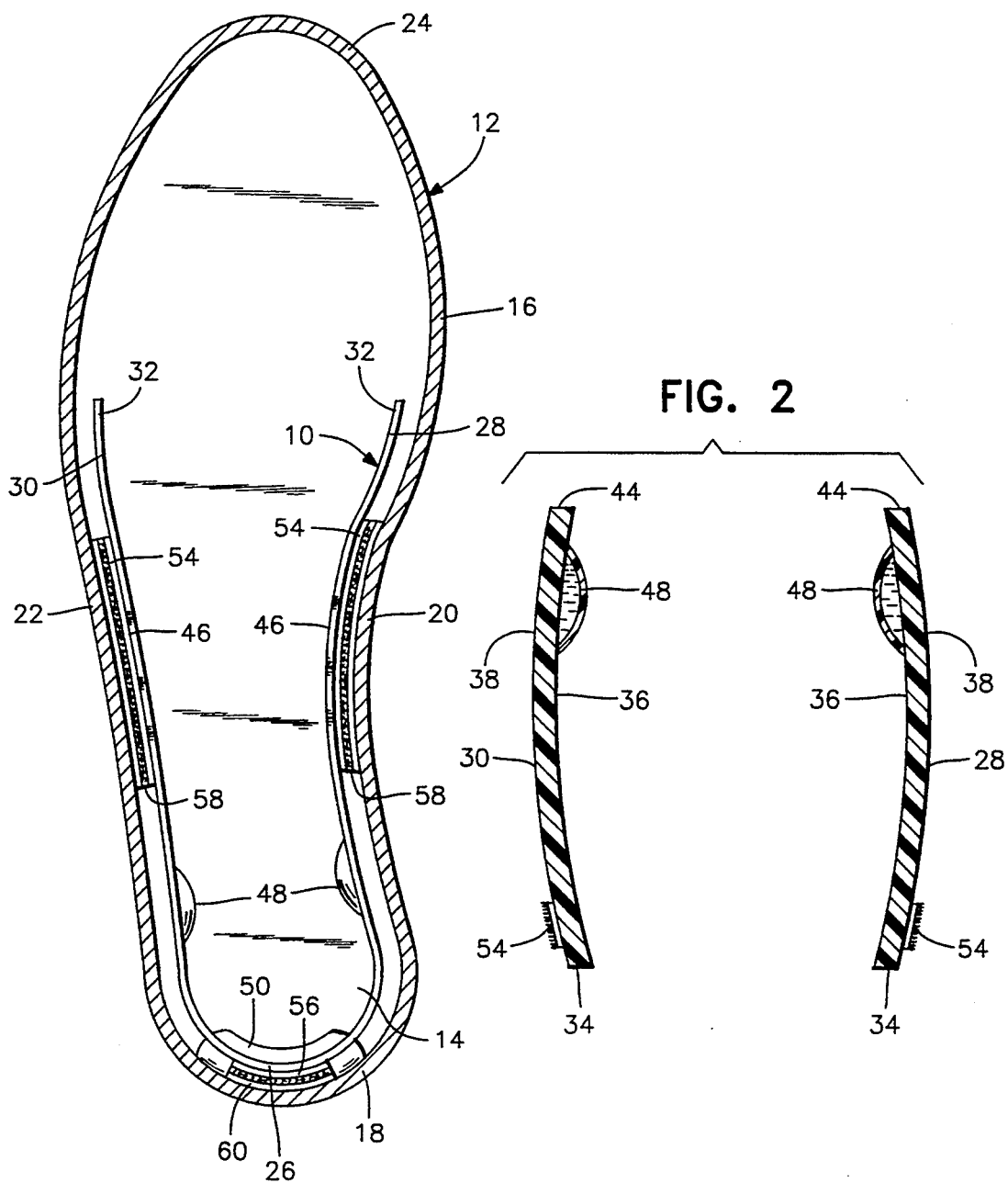

REMOVABLE, SHOE INTERIOR ANKLE BRACE

BACKGROUND OF THE INVENTION

1. Field of the Invention

This invention relates to a generally U-shaped insert for high-top or quarter-top athletic shoes and to be placed within an associated shoe with the bight portion of the insert at the heel of the shoe and the arms or legs of the insert extending forwardly along opposite sides of the corresponding shoe upper from the heel thereof. The insert is semirigid, includes multiple cushioning on the interior thereof and is designed to provide additional lateral support for the wearer's ankle, to provide increased performance such as leaping ability to the wearer of the associated shoe by maintaining the wearer's foot more stabilized and to support the wearer's foot in a manner such that the possibility of ligament damage as a result of over extension of the wearer's foot as to its mobility in any direction is reduced.

2. Description of Related Art

Various different forms of ankle and interior shoe bracing heretofore have been provided. Examples of these previously known apparatuses are disclosed in U.S. Pat. Nos. 3,237,319, 3,834,377, 4,385,456, 4,821,743 and 5,175,947.

However, these previously known apparatuses do not include the overall combination of structural and operational features incorporated in the instant invention.

SUMMARY OF THE INVENTION

The shoe insert of the instant invention comprises a generally U-shaped insert including a pair of generally parallel arms or legs interconnected at one pair of corresponding ends by a curved bight portion and the bight portion and legs are generally panel-like in configuration.

The insert is to be utilized in conjunction with high-top or quarter-top athletic shoes and is to be received therein with the curved bight portion of the insert disposed at the heel of the shoe and the legs of the insert extending forwardly from the heel along opposite side interior portions of the shoe. The forward ends of the arms or legs of the insert are relatively low in height as opposed to the rear ends of the arms and the curved bight portion of the insert, the lower margin of the curved bight portion of the insert being elevated relative to the lower margins of the arms or legs of the insert.

The upper margins of the rear ends of the arms or legs of the insert and the curved bight portion of the insert are disposed at an elevation above that elevation which would correspond to the malleolus bone area of an associated foot received within the corresponding shoe and the insert is provided with suitable padding. Further, the arms or legs of the insert are concavo-convex with their concave sides opposing each other.

The main object of this invention is to provide a removable insert for a quarter-top or high-top athletic shoe which, when removably secured within an athletic shoe of this type, will provide greater lateral support for a foot within the shoe.

Another object of this invention is to provide a shoe insert which will increase the performance capability of a person wearing a shoe having the insert of the instant invention therein by maintaining greater stability of the foot.

Another very important object of this invention is to provide an athletic shoe insert which will, in effect, increase the tensile strength of the ligaments in an associated foot and ankle.

A final object of this invention to be specifically enumerated herein is to provide an athletic shoe insert in accordance with the preceding objects and which will conform to conventional forms of manufacture, be of simple construction and easy to install so as to provide a device that will be economically feasible, long lasting and relatively trouble free in installation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of an insert constructed in accordance with the present invention in position within a shoe fragmentarily illustrated in phantom lines;

FIG. 2 is an enlarged fragmentary vertical sectional view taken substantially upon the plane indicated by the section line 22 of FIG. 1;

FIG. 3 is a horizontal sectional view of an athletic shoe having the insert of the instant invention operationally removably secured therein; and FIG. 4 is a fragmentary enlarged longitudinal vertical sectional view of the rear portion of an athletic shoe having the insert of the instant invention operationally removably supported therein and illustrating the heel padding of the insert.

DESCRIPTION OF THE PREFERRED EMBODIMENT

Referring now more specifically to the drawings the numeral 10 generally designates the insert of the instant invention and the numeral 12 generally designates a quarter-top athletic shoe.

The athletic shoe 12 includes a sole 14 and an upper 16 supported therefrom, the upper 16 including a rear heel portion 18, opposite side portions 20 and 22 and a toe portion 24. The upper 16 is more flexive than the shape retentive but flexible sole 14.

The insert 10 is generally U-shaped in configuration. In use, the insert 10 is horizontally disposed and includes an edge upstanding curved bight or heel portion 26 interconnecting the rear ends of a pair of opposite side, generally parallel and edge upstanding wings or arms 28 and 30. The wings or arms 28 and 30 include corresponding upper and lower margins 32 and 34 as well as corresponding inner and outer surfaces 36 and 38. The wings 28 and 30 are concavo-convex with their concave sides opposing each other and the rear ends of the wings or arms 28 and 30 merge smoothly into the opposite ends of the curved bight or heel portion 26, the heel portion 26 including upper and lower margins 40 and 42.

It may be seen from FIG. 1 of the drawings that the lower margin 42 is elevated appreciably above the lower margins 34. Further, the rear ends of the upper margins 32 are elevated as at 44 relative to the remainder of the upper margins 32 and the upper margin 40 is substantially coextensive with the rear ends 44 of the upper margins 32.

It may also be seen from FIG. 1 of the drawings that the longitudinal midportions of the upper margins 32 include rounded upwardly opening notches 46 formed therein and that the notches 46 are between ⅓ and ½ the height of the longitudinal central portions of the wings or arms 30 and 32 in which the notches 46 are formed.

The insert 10 is constructed of shape retentive but slightly flexive plastic or similar material and the inner surfaces 36 of the rear ends of the wings or arms 28 and 30 include cushioning means 48 secured thereto in the form of jell filled flexible cushion envelopes. Further, the inner surface of the bight or heel portion 26 includes similar cushioning means 50 in the form of a jell filled flexible envelope, a portion of the cushioning means or jell filled envelope 50 lapping under and at least slightly upwardly over the outer surface of the lower margin 42. The envelopes 48 and 50 may be constructed of any suitable flexible and fluid impervious material such as rubber, plastic or silicone.

The outer surfaces 38 of the wings or arms 30 and 32 include thistle-type fastening strips 54 supported therefrom and the outer surface of the bight or heel portion 26 includes a similar thistle-type fastening strip 56 secured thereto.

The insert 10 is positioned within the athletic shoe 12 with the bight or heel portion 26 thereof closely opposing the heel portion 18 of the shoe 12. The interior of the side portions 20 and 22 of the upper 16 include thistle-type fastening strips 58 secured thereto and with which the fastening strips 54 are releasably engaged and the inner surface of the heel portion 18 includes a thistle-type fastening strip 60 secured thereto with which the fastening strip 56 is removably engaged. In this manner, the fastening strips 54, 56, 58 and 60 removably secure the insert 10 within the upper 16.

The cushioning means 48 are positioned on the inner surfaces of the rear ends of the wings or arms 28 and 30 for directly opposing the malleolus bone areas of a foot received within the athletic shoe 12 so as to offer impact protection to the malleolus bone areas from impact thereon from exteriorly of the athletic shoe 12 and also for comfort measures.

Also, the upper portions of the rear ends of the wings or arms 32 of the insert 10 offer lateral support against excessive inturning of the associated foot about its longitudinal axis, such as some times causes serious sprained ankles, and the notches 46 allow some upward flexure of those portions of the wings or arms 30 and 32 disposed forwardly of the notches 46 relative to the rear ends of the wings or arms 30 and 32 and also flexure of the forward portions of the wings or arms 30 and 32 about opposite side portions of the associated foot to provide even further stability to the foot.

The wings or arms 28 and 30 are quite stiff and thereby resist, in conjunction with the associated athletic shoe 12, excessive lateral spreading of the bones of the foot forward of the ankle to thereby increase the stability of the foot and to allow the muscles of the foot to exert greater leaping forces. Still further, the overall reinforcement of the quarter-top athletic shoe 12 worn by a person increases the resistance of the associated foot against hyperflexure of the type that causes ligament damage to the foot and/or ankle.

The amount of elevation of the rear ends 44 of the upper margins 32 relative to the central and forward portions of the upper margins 32 will be determined by whether the insert 10 is to be utilized in a quarter-top shoe or a high top shoe. However, in any instance, the rear ends 44 will be appreciably elevated above the central and forward ends of the upper margins 32.

The elevation and padding of the lower margin 42 of the bight or heel portion 26 is important in that it prevent pinching of the heel of the wearer of the athletic shoe 12 and also cushions the achilles tendon area of the associated foot. Further, by positioning the fastening strips 54 along the central and rear portions of the wings or arms 28 and 30, maximum stability of the insert within the athletic shoe 12 is achieved between opposing areas of the wings or arms 28 and 30 of the insert 10 and the opposing side portions 20 and 22 of the upper 16. Of course, by placing the fastening strip 56 on the bight or heel portion 26 of the insert 10, further stability of the insert 10 relative to the athletic shoe 12 is assured between those heel portions thereof it is not desired to have relative movement take place.

In addition to the cushioning means 48 and 50, the entire inner surface as well as the entire outer surface of the insert 10 may be coated with a resilient foam coating (not shown), but it is not desired to have such resilient foam coating beneath the cushioning means 48 and 50 or the strips 54 and 56. Further, the entire insert 10 may be foraminated not only to assist in securement of the strips 54 and 56 as well as the cushioning means 48 to the insert 10, but to also increase air circulation around the associated foot.

The foregoing is considered as illustrative only of the principles of the invention. Further, since numerous modifications and changes readily will occur to those skilled in the art, it is not desired to limit the invention to the exact construction and operation shown and described, and accordingly, all suitable modifications and equivalents may be resorted to, falling within the scope of the invention.

What is claimed as new is as follows:

1. An ankle brace insert for lining a high top or quarter-top shoe and adapted to provide lateral ankle support for a foot in said shoe and to thereby effectively increase resistance of the foot against ligament damage and to increase the stress capacity of the foot to enable greater forces to be exerted thereby when the shoe user is attempting a leap, said insert including horizontally elongated, generally parallel, panel-shaped edge upstanding wings having inner and outer surfaces and corresponding front and rear ends joined at their rear ends by an integral, curved and edge upstanding bight panel portion having inner and outer surfaces and opposite ends coextensive with the rear ends of said wings, said wings and bight panel portion each including upper and lower margins, at least the forward end portions of the upper margins of said wings being lower than the upper margin of said bight panel portion and the lower margin of said bight panel portion being higher than the lower margins of said wings, said insert wings and bight panel portion being constructed of stiff, but somewhat flexive material, at least some of the inner surface portions of said wings and bight panel portion having padding means thereover, said outer surfaces of said wings and bight panel portion including fastening means thereon for releasable securement of said insert within a high-top or quarter-top shoe.

2. The insert of claim 1 wherein the rear portions of the upper margins of said wings are elevated relative to the forward and central portions of said upper margins of said wings.

3. The insert of claim 2 wherein said padding means includes mid-height fluent material filled flexible material packs secured over the inner surfaces of the rear ends of said wings adapted to oppose the malleolus bone areas of a human foot having the heel portion thereof substantially seated against said inner surface of said bight panel portion.

4. The insert of claim 3 wherein said padding means includes a fluent material filled flexible material pad secured over at least the central portion of the lower margin of said bight panel portion.

5. The insert of claim 4 wherein the last mentioned pad also laps beneath said lower margin of said bight panel portion and at least slightly upwardly over said outer surface of said bight panel portion immediately above said lower margin of said bight panel portion.

6. The insert of claim 2 wherein said wings are slightly vertically concavo-convex with said upper and lower margins thereof curved slightly inwardly.

7. The insert of claim 6 wherein said central portions of said upper margins of said wings each include a rounded upwardly opening notch formed therein of a height between ⅓ and ½ the height of the corresponding wing forward end and center portion.

8. The insert of claim 1 wherein said fastening means comprises thistle-type fastening strips adapted for releasable anchoring engagement with coacting thistle-type fastening strips anchored within an associated shoe.

9. In combination with a shoe of at least quarter-top height and including an upper incorporating a rear heel portion and opposite side side walls extending forwardly from said heel portion, an insert including horizontally elongated, generally parallel and panel-shaped edge upstanding wings having inner and outer surfaces and corresponding front and rear ends and joined at their rear ends by an integral, curved and edge upstanding bight panel portion having inner and outer surfaces and opposite ends coextensive with the rear ends of said wings, said insert being disposed in said upper with said bight panel portion conforming to and spaced slightly forward of said heel portion and said wings extending along and closely opposing said opposite side walls immediately inward thereof, said wings and bight panel portion each including upper and lower margins, at least the forward end portions of the upper margins of said wings being lower than the upper margin of said bight panel portion and the lower margin of said bight panel portion being higher than the lower margins of said wings, said insert wings and bight panel portion being constructed of stiff, but somewhat flexive material, at least some of the inner surface portions of said wings and bight panel portion having padding means thereover, said outer surfaces of said wings and bight panel portion and the opposing inner surfaces of said opposite side walls and heel portion including coacting fastening means releasably stationarily securing said insert within said upper.

10. The combination of claim 9 wherein said rear portions of the upper margins of said wings are elevated relative to the forward and longitudinal central portions of said upper margins of said wings.

11. The combination of claim 10 wherein said padding means includes mid-height fluent material filled flexible material packs secured over the rear portions of the inner surfaces of said wings adapted to oppose the malleolus bone areas of a human foot disposed in said shoe and having the heel portion thereof substantially seated against said inner surface of said bight panel portion.

12. The insert of claim 11 wherein said padding means includes a fluent material filled flexible material pad secured over at least the central portion of the lower margin of said bight panel portion and lapped beneath said lower margin of said bight panel portion and slightly upwardly over said outer surface of said bight panel portion immediately above said lower margin thereof, whereby the portion of the fluent material filled flexible material pad carried by the lower margin of said bight panel portion will function to pad the opposing heel of a human foot relative to the insert and the inner surface of the heel of said upper relative to said lower margin of said bight panel portion.

* * * * *